United States Patent
Cantat et al.

(10) Patent No.: US 8,877,971 B2
(45) Date of Patent: Nov. 4, 2014

(54) METHOD FOR PREPARING FORMAMIDE COMPOUNDS

(75) Inventors: Thibault Cantat, Issy les Moulineaux (FR); Christophe Gomes, Antony (FR); Olivier Jacquet, Orsay (FR)

(73) Assignee: Commissariat a l'Energie Atomique et aux Energies Alternatives, Paris (FR)

(*) Notice: Subject to any disclaimer, the term of this patent is extended or adjusted under 35 U.S.C. 154(b) by 0 days.

(21) Appl. No.: 13/805,899

(22) PCT Filed: Apr. 4, 2012

(86) PCT No.: PCT/IB2012/051667
§ 371 (c)(1),
(2), (4) Date: Jul. 12, 2013

(87) PCT Pub. No.: WO2012/137152
PCT Pub. Date: Oct. 11, 2012

(65) Prior Publication Data
US 2014/0018576 A1   Jan. 16, 2014

(30) Foreign Application Priority Data

Apr. 4, 2011 (FR) .................................... 11 52888
May 16, 2011 (FR) .................................... 11 54246

(51) Int. Cl.
| | | |
|---|---|---|
| C07C 231/10 | (2006.01) | |
| C07D 265/30 | (2006.01) | |
| C07C 249/02 | (2006.01) | |
| C07D 231/12 | (2006.01) | |
| C07D 233/58 | (2006.01) | |
| C07D 251/28 | (2006.01) | |
| C07C 249/16 | (2006.01) | |
| C07D 243/28 | (2006.01) | |
| C07D 233/06 | (2006.01) | |
| C07D 249/16 | (2006.01) | |
| C07D 249/08 | (2006.01) | |
| C07D 249/02 | (2006.01) | |
| C07D 241/04 | (2006.01) | |
| C07D 295/185 | (2006.01) | |
| C07C 241/04 | (2006.01) | |

(52) U.S. Cl.
CPC ............ *C07C 231/10* (2013.01); *C07C 249/02* (2013.01); *C07D 231/12* (2013.01); *C07D 233/58* (2013.01); *C07D 251/28* (2013.01); *C07C 249/16* (2013.01); *C07D 243/28* (2013.01); *C07D 233/06* (2013.01); *C07D 249/16* (2013.01); *C07D 249/08* (2013.01); *C07D 249/02* (2013.01); *C07D 241/04* (2013.01); *C07D 295/185* (2013.01); *C07C 241/04* (2013.01)
USPC ........................... 564/132; 544/106; 544/170

(58) Field of Classification Search
USPC ................... 564/132; 544/106, 170
See application file for complete search history.

(56) References Cited

U.S. PATENT DOCUMENTS

2012/0071690 A1*  3/2012  Pazicky et al. ............... 564/132

FOREIGN PATENT DOCUMENTS

| EP | 0 652 202 A1 | 5/1995 |
| GB | 783 582 A | 9/1957 |
| JP | 52 036617 A | 3/1977 |
| JP | 56 099450 A | 8/1981 |
| JP | 62 255456 A | 11/1987 |
| JP | 62 266456 A | 11/1987 |

OTHER PUBLICATIONS

Rohr et al, Applied Catalysts A: General, 296(2), 238-250, 2005.*
International Search Report and Written Opinion for Application No. PCT/IB2012/051667 dated Oct. 31, 2012.
Dell'Amico, D. B. et al., *Converting Carbon Dioxide Into Carbamato Derivatives*, Chem. Rev. 103 (2003) 3857-3897.
Dibenedetto, A. et al., *Reaction of Silylalkylmono- and Silylalkyldiamines with Carbon Dioxide: Evidence of Formation of Inter- and Intra-Molecular Ammonium Carbamates and Their Conversion Into Organic Carbamates of Industrial Interest Under Carbon Dioxide Catalysis*, Green Chemistry 4 (2002) 439-443.
Gomes, C. D. N. et al., *A Diagonal Approach to Chemical Recycling of Carbon Dioxide: Organocatalytic Transformation for the Reductive Functionalization of $CO_2$*, Agnew. Chem. Int. Ed. 50 (2011) 1-6.
Jacquet, O. et al., *Recycling of Carbon and Silicon Wastes: Room Temperature Formylation of N-H Bonds Using Carbon dioxide and Polymethylhydrosiloxane*, Journal of the American Chemical Society, 134 (2012) 2934-2937.
Dinsmore, C. J. et al., Organic Letters, 2004, vol. 6, No. 17 2885-2888.
Ekhato, I. V. et al., J., Label Compd. Radiopharm, 2011, 54, 202-205.
Federsel, C. et al., Angew. Chem. Int. Ed. 2010, 49, 9777.
Greenberg, A. B. et al., The Amide Linkage: Structural Significance in Chemistry, Biochemistry, and Materials Science, Wiley-Interscience, Hoboken, NJ 2002.
Groves, J. T. et al., J. Am. Chem. Soc. 1988, 110, 8443-8452.
Ho, J. Z. et al., Helvetica Chimica Acta, 2005, 88, 1040.
Jessop, P. G. et al., Journal of the American Chemical Society 1994, 116, 8851.
Jessop, P. G. et al., Journal of the American Chemical Society 1996, 118, 344.
Kayaki, Y. et al., Chemistry Letters 2001, 1016.
Kayaki, Y. et al., Advanced Synthesis & Catalysis 2003, 345, 175.

(Continued)

*Primary Examiner* — Shailendra Kumar
(74) *Attorney, Agent, or Firm* — Alston & Bird LLP (57) ABSTRACT

The present invention relates to a method for preparing formamide compounds using carbon dioxide, and to the use of said method for manufacturing vitamins, pharmaceutical products, adhesives, acrylic fibers, synthetic leathers, pesticides and fertilizers. The invention also relates to a method for manufacturing vitamins, pharmaceutical products, adhesives, acrylic fibers, synthetic leathers, pesticides and fertilizers which includes a step of preparing formamide compounds by the method according to the invention.

20 Claims, 5 Drawing Sheets

(56) References Cited

OTHER PUBLICATIONS

Kim, Y. et al., J. Org. Chem. 1991, 56, 4435-4439.
Kochina, T. A. et al., Russian Journal of General Chemistry, vol. 72, No. 8, 2002, 1222-1224.
Krocher, O. et al., High Pressure Chemical Engineering 1996, 12, 91.
Krocher, O. et al., Chemical Communications 1997, 453.
Liu, J. et al., Chemical Communications 2010, 46, 5770.
Liu, F. C. et al. Chemical Communications 2001, 433.
Morris, A. J. et al., *Accounts Chem Res* 2009, 42, 1983.
Munshi, P. et al., Tetrahedron Letters 2003, 44, 2725.
Pleiss, U. et al., *Synthesis and Applications of Isotopically Labelled Compounds,* vol. 7, Wiley-VCH, 2001.
Riduan, S. N. et al., *Angewandte Chemie—International Edition* 2009, 48, 3322.
Sakakura, T. et al., *Chem Rev* 2007, 107, 2365.
Schmid, L. et al., Chemical Communications 1999, 2303.
Schreiner, S. et al., Inorganica Chimica Acta 1988, 147, 139.
Schreinder, S. et al., Journal of the Chemical Society—Chemical Communications 1988, 602.
Shishigin, E. A. et al., Russian Journal of General Chemistry, vol. 75, No. 1, 2005, 152.
Vaska, L. et al., Journal of Molecular Catalysis 1989, 52, L11.
Voges, J. R. et al., *Preparation of Compounds Labeled with Tritium and Carbon-14,* Wiley-VCH, Chippenham (UK) 2009.
Yu, J. Y. et al., Inorganica Chimica Acta 1990, 170, 145.
Panorama des voies de valorization due $CO_2$, ADEME, Jun. 2010, http://www2.ademe.fr/servlet/getDoc?cid=96&m=3&id=72052&p1=30&ref=12441.

\* cited by examiner

METHOD FOR PREPARING FORMAMIDE COMPOUNDS

This application is a 371 of PCT/IB2012/051667, filed Apr. 4, 2012.

FIELD

The present invention relates to a process for preparing formamide compounds using carbon dioxide, and the use of this process in the manufacture of vitamins, pharmaceutical products, glues, acrylic fibers, and synthetic leathers, pesticides, and fertilizers.

It also relates to a method for manufacturing vitamins, pharmaceutical products, glues, acrylic fibers, synthetic leathers, pesticides, and fertilizers, comprising a step of preparing formamide compounds by the process according to the invention.

BACKGROUND

The utilization of useful $CO_2$ as a carbon source for the production of chemical consumables is a prime challenge with the aim both of decreasing its accumulation in the atmosphere and of curtailing our dependence on fossil fuels.

The greatest challenge facing scientists and industrialists is to recycle $CO_2$ that is, to develop reactions which allow the production of chemical compounds, examples being fuels, polymeric plastics, drugs, detergents, and bulk molecules, which have traditionally been obtained by petrochemical methods. The technical difficulty lies in the development of chemical reactions which functionalize the $CO_2$ while reducing the carbon center (i.e., by replacing the C—O bonds in the $CO_2$ with C—H or C—C bonds).

Figure 1:
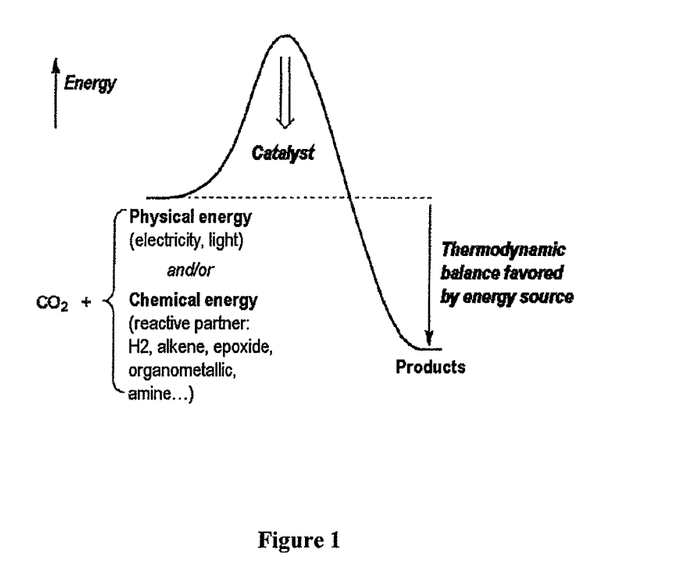
FIG. 1 shows the thermodynamic stability of carbon dioxide, and the need to employ an external energy source in order to promote the thermodynamic balance of the chemical conversion and the conversion of $CO_2$ into new chemical consumables.

Owing to the high thermodynamic stability of carbon dioxide, converting it into new chemical consumables necessarily involves an external energy source, so as to promote the thermodynamic balance of the chemical conversion, which is shown in FIG. 1.

The entirety of the efforts made by the scientific community is presently focused on the use of electricity or light to perform the electroreduction or photoreduction of $CO_2$ into formic acid, methanal, methanol, and methane (Morris, A. J., Meyer, G. J., Fujita, E., Accounts Chem Res 2009, 42, 1983). Accordingly, this field of research is the subject of intense international competition.

A recent article describes how the use of silane compounds makes it possible to reduce $CO_2$ under organocatalytic conditions (Riduan, S, N., Zhang, Y. G., Ying, J. Y., Angewandte Chemie—International Edition 2009, 48, 3322). In this case, the silane compound is the high-energy reactive species, and the use of the catalyst promotes the kinetic balance. The authors describe the formation of silyl products of formyl (SiOCHO), acetal (SiOCH$_2$OSi), and methoxy (SiOCH$_3$) types. Although this strategy is justified by the importance of the uses of reduction products of $CO_2$ in the chemical industry (HCOOH, H$_2$CO, CH$_3$OH), it should nevertheless be noted that these molecules are currently used on a scale which remains very low in relation to the amount of useful $CO_2$ available. In other words, if these molecules were to be produced exclusively from $CO_2$, they would allow the utilization, on the basis of the current market, of only 3.4% of the useful $CO_2$ produced each year (2.5 Gt/year) (Panorama des voies de valorisation du $CO_2$, ADEME, June 2010, http://www2.ademe.fr/servlet/getDoc?cid=96&m=3&id=72052&p1=30&ref=12441). It is therefore necessary to look at diversifying the nature and number of chemical consumables that are obtainable from $CO_2$.

Another strategy in converting $CO_2$ into new chemical consumables involves using a reactive chemical partner (high in energy) to promote the thermodynamic balance of the chemical conversion of $CO_2$. This strategy is presently not widely represented within the scientific landscape, but it will, eventually, allow a considerable expansion in the range of molecules available from $CO_2$. The only industrial process based on this approach is the synthesis of urea obtained by condensing ammonia with $CO_2$, as indicated in equation 1 below (Sakakura, T., Choi, J. C., Yasuda, H., Chem Rev 2007, 107, 2365).

(equation 1)

Following the same principle, the synthesis of polycarbonates by $CO_2$/epoxide copolymerization is undergoing industrialization, as indicated in equation 2 below (Panorama des voies de valorisation du $CO_2$, ADEME, June 2010, http://www2.ademe.fr/servlet/getDoc?cid=96&m=3&id=72052&p1=30&ref=12441).

(equation 2)

In these two syntheses (equations 1 and 2), there is no formal reduction of the carbon center of $CO_2$.

Still with the aim of obtaining new chemical compounds, it is possible to consider converting the $CO_2$ into formamide compounds. Formamide compounds are a class of chemical compounds which are important in the chemical industry, in which they are presently used as solvents, reagents, and precursors to plastics (The Amide Linkage: Structural Significance in Chemistry, Biochemistry, and Materials Science, Greenberg, A. B., C. M., Liebman, J. F.; Wiley-Interscience: Hoboken, N.J., 2002). Formamide compounds (of general formula $R^1R^2NCHO$) are generally synthesized by condensing amines with formic acid.

N,N-Dimethylmethanamide (also called dimethylformamide), which is the most commonly used formamide compound, given that it serves as a polar solvent, is produced industrially by reacting dimethylamine with carbon monoxide under catalytic conditions (The Amide Linkage: Structural Significance in Chemistry, Biochemistry, and Materials Science, Greenberg, A. B., C. M., Liebman, J. F.; Wiley-Interscience: Hoboken, N.J., 2002).

Formamide compounds may also be obtained starting from carbon dioxide instead of carbon monoxide, which is toxic. This alternative pathway rests on the synthesis of the formamide compounds by reaction of carbon dioxide, dihydrogen, and an amine in the presence of transition metal complexes as catalyst (Schreiner, S., Yu, J. Y.; Vaska, L., Inorganica Chimica Acta 1988, 147, 139; Schreiner, S., Yu, J. Y., Vaska, L. *Journal of the Chemical Society—Chemical Communications* 1988, 602; Vaska, L., Schreiner, S., Felty, R. A., Yu, J. Y., *Journal of Molecular Catalysis* 1989, 52, L11; Yu, J. Y., Schreiner, S., Vaska, L. *Inorganica Chimica Acta* 1990, 170, 145; Jessop, P. G., Hsiao, Y., Ikariya, T., Noyori, R., *Journal of the American Chemical Society* 1994, 116, 8851; Jessop, P. G., Hsiao, Y., Ikariya, T., Noyori, R. *Journal of the American Chemical Society* 1996, 118, 344; Munshi, P., Heldebrant, D. J., McKoon, E. P., Kelly, P. A., Tai, C. C., Jessop, P. G., *Tetrahedron Letters* 2003, 44, 2725); Schmid, L., Rohr, M., Baiker, A., *Chemical Communications* 1999, 2303; Federsel, C., Boddien, A., Jackstell, R., Jennerjahn, R., Dyson, P. J., Scopelliti, R., Laurenczy, G., Beller, M., *Angew. Chem. Int. Ed.* 2010, 49, 9777; Liu, J., Guo, C., Zhang, Z., Jiang, T., Liu, H., Song, J., Fan, H., Han, B., *Chemical Communications* 2010, 46, 5770. This pathway has numerous drawbacks, more particularly the following:

- the choice of starting amine is very limited: dimethylamine, diethylamine, piperidine, and aniline (Schreiner, S., Yu, J. Y.; Vaska, L., *Inorganica Chimica Acta* 1988, 147, 139; Schreiner, S., Yu, J. Y., Vaska, L. *Journal of the Chemical Society—Chemical Communications* 1988, 602; Vaska, L., Schreiner, S., Felty, R. A., Yu, J. Y., *Journal of Molecular Catalysis* 1989, 52, L11; Yu, J. Y., Schreiner, S., Vaska, L. *Inorganica Chimica Acta* 1990, 170, 145; Jessop, P. G., Hsiao, Y., Ikariya, T., Noyori, R., *Journal of the American Chemical Society* 1994, 116, 8851; Jessop, P. G., Hsiao, Y., Ikariya, T., Noyori, R. *Journal of the American Chemical Society* 1996, 118, 344; Munshi, P., Heldebrant, D. J., McKoon, E. P., Kelly, P. A., Tai, C. C., Jessop, P. G., *Tetrahedron Letters* 2003, 44, 2725); Schmid, L., Rohr, M., Baiker, A., *Chemical Communications* 1999, 2303; Federsel, C., Boddien, A., Jackstell, R., Jennerjahn, R., Dyson, P. J., Scopelliti, R., Laurenczy, G., Beller, M., *Angew. Chem. Int. Ed.* 2010, 49, 9777; Liu, J., Guo, C., Zhang, Z., Jiang, T., Liu, H., Song, J., Fan, H., Han, B., *Chemical Communications* 2010, 46, 5770;
- the $CO_2$ and $H_2$ pressure required is generally high: from 100 to 250 bar and at 100° C. (except for a platinum system which is active at ambient temperature under a pressure of 1 bar, described by Schreiner, S., Yu, J. Y., Vaska, L., *Journal of the Chemical Society—Chemical Communications* 1988, 602);
- this pathway requires the use of transition metal complexes which are often expensive (Ir, Ru, Rh, Pt, Cu, Fe);
- the use of an organic solvent is generally required, except for a few isolated examples of reactions in supercritical $CO_2$ (Jessop, P. G., Hsiao, Y., Ikariya, T., Noyori, R., *Journal of the American Chemical Society* 1994, 116, 8851; Jessop, P. G., Hsiao, Y.; Ikariya, T., Noyori, R., *Journal of the American Chemical Society* 1996, 118, 344; Krocher, O., Koppel, R. A., Baiker, A., *High Pressure Chemical Engineering* 1996, 12, 91; Kayaki, Y., Suzuki, T., Ikariya, T. *Chemistry Letters* 2001, 1016; Liu, F. C., Abrams, M. B., Baker, R. T., Tumas, W., *Chemical Communications* 2001, 433; Kayaki, Y., Shimokawatoko, Y., Ikariya, T., *Advanced Synthesis & Catalysis* 2003, 345, 175), and of one example in ionic liquid (Liu, F. C., Abrams, M. B., Baker, R. T., Tumas, W., *Chemical Communications*, 2001, 433), and of one example without solvent (Krocher, O., Koppel, R. A., Baiker, A., *Chemical Communications* 1997, 453);
- the addition of additives (carbon, oxygen, or nitrogen bases) is necessary in order to accelerate the reaction or improve the yields and selectivities (Munshi, P., Heldebrant, D. J., McKoon, E. P., Kelly, P. A.; Tai, C. C., Jessop, P. G. *Tetrahedron Letters* 2003, 44, 2725).

In the context of the synthesis of formamide compounds using carbon dioxide, the technical challenge to be answered is to couple the functionalization of the carbon dioxide with a step of chemical reduction. In order to maximize the energy yield of such a conversion, it is necessary to develop reactions having a limited number of steps (ideally just one), and catalyzed, in order to prevent energy losses of kinetic order.

Moreover, labeled formamide compounds, incorporating stable isotopes and/or radio isotopes, is of particular interest in numerous sectors, such as, for example, in the life sciences (study/elucidation of enzymatic mechanisms, biosynthetic mechanisms, in biochemistry, etc.), environmental sciences (tracing of wastes, etc.), research (study/elucidation of reaction mechanisms), or else research and development of new pharmaceutical and therapeutic products. Accordingly, developing a synthesis for preparing labeled formamide compounds meeting the requirements indicated above can respond to a genuine need.

There is therefore a genuine need for a process for preparing formamide compounds by conversion of $CO_2$ that overcomes the drawbacks of the prior art, said process allowing the functionalization of the carbon dioxide to be coupled with a step of chemical reduction.

In particular, a genuine need exists for a process which produces the formamide compounds in a single step and with an excellent selectivity, from $CO_2$ and amines, under catalytic conditions, and in the presence of a compound which ensures the reduction of $CO_2$.

Moreover, there exists a genuine need to have a process which produces, in a single step and with an excellent selectivity, labeled formamide compounds incorporating stable isotopes and/or radio isotopes, starting from labeled reagents such as, for example, labeled $CO_2$ and/or labeled amines, under catalytic conditions and in the presence of a compound which ensures the reduction of $CO_2$.

SUMMARY

The specific aim of the present invention is to meet these needs by providing a process for preparing formamide compounds of formula (I):

in which
R$^1$ and R$^2$ represent independently of one another a hydrogen atom, an alkyl group, an alkenyl group, an alkynyl group, an aryl group, a heteroaryl group, a heterocycle, a silyl group, a siloxy group, an amino group, an aldimine of formula —N=CHR$^6$, or a ketimine of formula —N=CR$^6$R$^7$, said alkyl, alkenyl, alkynyl, aryl, heteroaryl, heterocycle, silyl, siloxy, and amino groups being optionally substituted, or
R$^1$ and R$^2$, together with the nitrogen atom to which they are bonded, form an optionally substituted heterocycle, or
R$^1$ and R$^2$, with the nitrogen atom to which they are bonded, form a carbon-nitrogen double bond (N=C), thus giving an aldimine of formula —N=CHR$^6$ or a ketimine of formula —N=CR$^6$R$^7$, and

R$^6$ and R$^7$ represent independently of one another a hydrogen atom, an alkyl group, an alkenyl group, an akynyl group, an aryl group, a heteroaryl group, a heterocycle, a silyl group, a siloxy group, or an amino group, said alkyl, alkenyl, akynyl, aryl, heteroaryl, heterocycle, silyl, siloxy, and amino groups being optionally substituted, characterized in that an amine of formula (II) in which R$^1$ and R$^2$ are as defined above, (II)

is reacted with CO$_2$ in the presence of a catalyst and with a silane compound of formula (III)

(III)

in which

R$^3$, R$^4$ and R$^5$ represent independently of one another a hydrogen atom, a halogen atom, a hydroxyl group, an alkyl group, an alkenyl group, an alkynyl group, an alkoxy group, a silyl group, a siloxy group, an aryl group, or an amino group, said alkyl, alkenyl, alkynyl, alkoxy, silyl, siloxy, aryl, and amino groups being optionally substituted, or R$^5$ is as defined above and R$^3$ and R$^4$, together with the silicon atom to which they are bonded, form an optionally substituted, silyl-containing heterocycle.

The advantage of the process of the invention is to allow the conversion of the CO$_2$ into formamide compounds with a wide selection of amines of formula (II) (primary, secondary, aromatic, aliphatic amines, etc.). In this process, said amines serve essentially to functionalize the CO$_2$, and the silane compounds of formula (III) ensure the reduction of CO$_2$, under catalytic conditions.

The formamide compounds are therefore obtained with an excellent yield (of the order of 60% to 100%, for example) and with an excellent selectivity (100% of formamide compounds isolated).

In the context of the present invention, the yield is calculated relative to the amount of amine of formula (II) initially introduced, on the basis of the amount of formamide isolated:

Yield=$n$(amide)/($n$(amide)+$n$(amine)) where $n$ is the amount of substance

In the context of the present invention, the selectivity is based on the nature of the products formed from the amine of formula (II). Since the formamide compounds of formula (I) are the only nitrogen-containing products formed during the process of the invention, the selectivity is total.

"Alkyl" in the sense of the present invention means a linear, branched, or cyclic, saturated or unsaturated, optionally substituted carbon radical containing 1 to 12 carbon atoms. Saturated linear or branched alkyl includes, for example, methyl, ethyl, propyl, butyl, pentyl, hexyl, heptyl, octyl, nonyl, decyl, undecyl, and dodecanyl radicals and their branched isomers. Cyclic alkyl includes cyclopropyl, cyclobutyl, cyclopentyl, cyclohexyl, bicyclo[2.1.1]hexyl, and bicyclo[2.2.1]heptyl radicals. Unsaturated cyclic alkyls include, for example, cyclopentenyl, and cyclohexenyl. Unsaturated alkyls, which are also called "alkenyl" or "alkynyl", contain, respectively, at least one double or triple bond. This may include, for example, ethylenyl, propylenyl, butenyl, pentenyl, hexenyl, acetylenyl, propynyl, butynyl, pentynyl, and hexynyl radicals and their branched isomers. The alkyl group, including for the purposes of the invention alkenyl and alkynyl groups, may be optionally substituted by one or more hydroxyl groups; one or more alkoxy groups; one or more halogen atoms selected from fluorine, chlorine, bromine, and iodine atoms; one or more nitro groups (—NO$_2$); one or more nitrile groups (—CN); one or more aryl groups, with the alkoxy and aryl groups as defined in the context of the present invention.

The term "aryl" denotes, generally, a cyclic aromatic substituent containing from 6 to 20 carbon atoms. In the context of the invention, the aryl group may be mono- or polycyclic. As an indication, the groups phenyl, benzyl, and naphthyl are included. The aryl group may be optionally substituted by one or more hydroxyl groups, one or more alkoxy groups, one or more halogen atoms selected from fluorine, chlorine, bromine, and iodine atoms, one or more nitro groups (—NO$_2$), one or more nitrile groups (—CN), one or more alkyl groups, one or more aryl groups, with the alkoxy, alkyl, and aryl groups as defined in the context of the present invention.

The term "heteroaryl" denotes, generally, a mono- or polycyclic aromatic substituent containing from 5 to 10 members, including at least 2 carbon atoms, and at least one heteroatom selected from nitrogen, oxygen, or sulfur. The heteroaryl group may be mono- or polycyclic. As in indication, the groups furyl, benzofuranyl, pyrrolyl, indolyl, isoindolyl, azaindolyl, thiophenyl, benzothiophenyl, pyridyl, quinolinyl, isoquinolyl, imidazolyl, benzimidazolyl, triazolyl, pyrazolyl, oxazolyl, isoxazolyl, benzoxazolyl, thiazolyl, benzothiazolyl, isothiazolyl, pyridazinyl, pyrimidinyl, pyrazinyl, triazinyl, cinnolinyl, phtalazinyl, quinazolinyl, 1,1-diphenylhydrazinyl, and 1,2-diphenylhydrazinyl are included. The heteroaryl group may be optionally substituted by one or more hydroxyl groups, one or more alkoxy groups, one or more halogen atoms selected from fluorine, chlorine, bromine, and iodine atoms, one or more nitro groups (—NO$_2$), one or more nitrile groups (—CN), one or more aryl groups, one or more alkyl groups with the alkyl, alkoxy, and aryl groups as defined in the context of the present invention.

The term "alkoxy" signifies an alkyl group, as defined above, which is bonded by an oxygen atom (—O-alkyl).

The term "heterocycle" denotes, generally, a mono- or polycyclic substituent containing 5 to 10 members, which is saturated or unsaturated and contains from 1 to 4 heteroatoms selected independently of one another from nitrogen, oxygen, and sulfur. As an indication, the substituents morpholinyl, piperidinyl, piperazinyl, pyrrolidinyl, imidazolyl, imidazolidinyl, imidazolinyl, pyrazolidinyl, tetrahydrofuranyl, tetrahydropyranyl, tetrahydropyrimidinyl, triazolyl, pyrazolyl, thianyl, oxazolidinyl, isoxazolidinyl, thiazolidinyl, and isothiazolidinyl are included. The heterocycle may be optionally substituted by one or more hydroxyl groups, one or more alkoxy groups, one or more aryl groups, one or more halogen atoms selected from fluorine, chlorine, bromine, and iodine atoms, one or more nitro groups (—NO$_2$), one or more nitrile groups (—CN), one or more alkyl groups, with the alkyl, alkoxy, and aryl groups as defined in the context of the present invention.

By halogen atom is meant an atom selected from fluorine, chlorine, bromine, or iodine atoms.

A "silyl" group is a group of formula [—Si(X)$_3$] in which each X independently of one another is selected from a hydrogen atom, one or more halogen atoms selected from fluorine, chlorine, bromine, or iodine atoms, one or more alkyl groups, one or more alkoxy groups, one or more aryl groups, and one or more siloxy groups, with the alkyl, alkoxy, aryl, and siloxy groups as defined in the context of the present invention.

A "siloxy" group is a silyl group, as defined above, which is bonded by an oxygen atom (—O—Si(X)$_3$).

In the sense of the invention, "silyl-containing heterocycle" means a mono- or polycyclic substituent which contains from 5 to 15 members and is saturated or unsaturated, and which contains at least one silicon atom and optionally at least one other heteroatom selected from nitrogen, oxygen, or sulfur. Said silyl-containing heterocycle may optionally be substituted by one or more hydroxyl groups; one or more alkyl groups; one or more alkoxy groups; one or more halogen atoms selected from fluorine, chlorine, bromine, and iodine atoms; one or more aryl groups, with the alkyl, alkoxy, and aryl groups as defined in the context of the present invention. Silyl-containing heterocycles may include, for example, 1-silacyclo-3-pentene or 1-methyl-1,1-dihydrido-2,3,4,5-tetraphenyl-1-silacyclopentadiene, according to the formulae below.

1-silacyclo-3-pentene 1-methyl-1-hydrido-2, 3, 4, 5-tetraphenyl-1-silacyclopentadiene Mention may also be made, for example, of methylsiloxane, 1-phenyl-1-silacyclohexane, 1-sila-bicyclo[2.2.1]heptane, 1-methyl-1-silacyclopentane, and 9,9-dihydro-5-silafluorene, which corresponds to the formulae below.

1-phenyl-1-silacyclohexane methyl siloxane 1-sila-bicyclo[2, 2, 1] heptane 1-methyl-1-silacyclopentane 9, 9-dihydro-5-silafluorene An "amino" group is a group of formula —NR$^6$R$^7$, in which:
R$^6$ and R$^7$ represent independently of one another a hydrogen atom, an alkyl group, an alkenyl group, an alkynyl group, an aryl group, a heteroaryl group, a heterocycle, a silyl group, or a siloxy group, with the alkyl, alkenyl, alkynyl, aryl, heteroaryl, heterocycle, silyl, and siloxy groups as defined in the context of the present invention; or
R$^6$ and R$^7$, together with the nitrogen atom to which they are bonded, form a heterocycle which is optionally substituted by one or more hydroxyl groups; one or more alkyl groups; one or more alkoxy groups; one or more halogen atoms selected from fluorine, chlorine, bromine, and iodine atoms; one or more nitro groups (—NO$_2$); one or more nitrile groups (—CN); one or more aryl groups; with the alkyl, alkoxy, and aryl groups as defined in the context of the present invention.

When R$^1$ and R$^2$, with the nitrogen atom to which they are bonded, form a carbon-nitrogen double bond (N=C), thereby giving an aldimine of formula —N=CHR$^6$ or a ketimine of formula —N=CR$^6$R$^7$, and when R$^6$ and R$^7$ represent independently of one another an alkyl group, an alkenyl group, an alkynyl group, an aryl group, a heteroaryl group, a heterocycle, a silyl group, a siloxy group, or an amino group, said alkyl, alkenyl, alkynyl, aryl, heteroaryl, heterocycle, silyl, siloxy, and amino groups as defined in the context of the present invention may be optionally substituted by one or more hydroxyl groups, one or more alkoxy groups, one or more aryl groups, one or more halogen atoms selected from fluorine, chlorine, bromine, and iodine atoms, one or more nitro groups (—NO$_2$), one or more nitrile groups (—CN), one or more alkyl groups, with the alkyl, alkoxy, and aryl groups as defined in the context of the present invention.

A catalyst in the sense of the invention is any compound capable of modifying, more particularly increasing, the rate of the chemical reaction in which it participates, and which is regenerated at the end of the reaction. This definition encompasses both catalysts, these being compounds which exert their catalytic activity with no need to undergo any modification or conversion, and compounds (also called precatalysts) which are introduced into the reaction mixture, where they are converted into a catalyst.

According to one preferred variant of the invention, in the amine of formula (II),
R$^1$ and R$^2$ represent independently of one another a hydrogen atom, an alkyl group, an aryl group, a heteroaryl group or an amino group, said alkyl, amino, aryl, and heteroaryl groups being optionally substituted, or
R$^1$ and R$^2$, together with the nitrogen atom to which they are bonded, form an optionally substituted heterocycle; or
R$^1$ and R$^2$, with the nitrogen atom to which they are bonded, form a carbon-nitrogen double bond (N=C), thus giving an aldimine of formula —N=CHR$^6$ or a ketimine of formula —N=CR$^6$R$^7$, in which R$^6$ and R$^7$ represent independently of one another a hydrogen atom, an alkyl group, an aryl group, a heteroaryl group, or a heterocycle, said alkyl, aryl, heteroaryl, and heterocycle groups being optionally substituted.

Preferably, in the amine of formula (II), R$^1$ and R$^2$ represent independently of one another a hydrogen atom; an alkyl group selected from methyl, ethyl, propyl, butyl, pentyl, hexyl, and heptyl groups or their branched isomers, and cyclohexyl groups; an aryl group selected from benzyl or phenyl; a heteroaryl group selected from imidazolyl or benzimidazolyl; an amino group of formula —NR$^6$R$^7$, in which R$^6$ and R$^7$ represent an aryl group selected from benzyl or phenyl, said aryl group being optionally substituted; or
R$^1$ and R$^2$, together with the nitrogen atom to which they are bonded, form a heterocycle containing from 5 to 6 members and selected from morpholine; piperidine; piperazine; pyrrolidine; oxazolidine; or isoxazolidine; and imidazole, more particularly 1H-imidazole; tetrahydropyrimidine, more particularly 1,4,5,6-tetrahydropyrimidine; triazolyl, and pyrazolyl, or

$R^1$ and $R^2$, with the nitrogen atom to which they are bonded, form a carbon-nitrogen double bond (N=C), thereby giving an aldimine of formula —N=CHR$^6$ or a ketimine of formula —N=CR$^6$R$^7$ in which $R^6$ and $R^7$ represent independently of one another an aryl group selected from benzyl or phenyl, said alkyl, alkoxy, and aryl group being optionally substituted.

According to another preferred variant of the invention, in the silane compound of formula (III), $R^3$, $R^4$ and $R^5$ represent independently of one another a hydrogen atom, an alkyl group, an alkoxy group, an aryl group, a silyl group, or a siloxy group, said alkyl, alkoxy, silyl, siloxy, and aryl groups being optionally substituted.

Preferably, in the silane compound of formula (III), $R^3$, $R^4$ and $R^5$ represent independently of one another
- a hydrogen atom;
- an alkyl group selected from methyl, ethyl, propyl, butyl, pentyl, hexyl, and heptyl groups or their branched isomers;
- an alkoxy group in which the alkyl group is selected from methyl, ethyl, propyl, butyl, pentyl, hexyl, and heptyl groups or their branched isomers;
- an aryl group selected from benzyl or phenyl groups;
- a silyl group of formula [—Si(X)$_3$] in which each X independently of one another is selected from a hydrogen atom, one or more halogen atoms selected from chlorine, bromine, or iodine atoms, one or more alkyl groups selected from methyl, ethyl, propyl, butyl, pentyl, hexyl, and heptyl groups or their branched isomers, one or more alkoxy groups in which the alkyl group is selected from methyl, ethyl, propyl, butyl, pentyl, hexyl, and heptyl groups or their branched isomers, and one or more siloxy groups in which the group —Si(X)$_3$ is as described in this embodiment.

The catalysts may be selected from organic catalysts or metal catalysts selected from metal complexes or salts. The organic catalysts have the advantage of obviating the toxicity problems which are generally observed for metal catalysts, and also the cost problems associated with the use of precious metals. In the process of the invention, the catalyst is preferably organic.

The organic catalysts are, generally speaking, organic bases selected from:
- nitrogen-containing bases, such as, for example, secondary or tertiary amines selected from triazabicyclodecene (TBD); N-methyltriazabicyclodecene (MeTBD), 1,8-diazabicyclo[5.4.0]undec-7-ene (DBU), trimethylamine, triethylamine, piperidine, 4-dimethylaminopyridine (DMAP), 1,4-diazabicyclo[2.2.2]octane (DABCO), proline, phenylalanine, a thiazolium salt, N-diisopropylethylamine (DIPEA or DIEA);
- phosphorus-containing bases, such as, for example, alkyl and aryl phosphines selected from triphenylphosphine, 2,2'-bis(diphenylphosphino)-1,1'-binaphthyl (BINAP), triisopropylphosphine; alkyl and aryl phosphonates selected from diphenyl phosphate, triphenyl phosphate (TPP), tri(isopropylphenyl) phosphate (TIPP), cresyl diphenyl phosphate (CDP), tricresyl phosphate (TCP); alkyl and aryl phosphates selected from di-n-butyl phosphate (DBP), tris-(2-ethylhexyl) phosphate, triethyl phosphate;
- carbon-containing bases for which protonation takes place on a carbon atom, such as, for example, an N-heterocyclic carbene such as a carbene obtained from an imidazolium salt selected from the salts of 1,3-bis(2,6-diisopropylphenyl)-1H-imidazol-3-ium (carbene A), 1,3-bis(2,6-diisopropylphenyl)-4,5-dihydro-1H-imidazol-3-ium (carbene C), 1,3-bis(2,4,6-trimethylphenyl)-1H-imidazol-3-ium (carbene B), 1,3-bis(2,4,6-trimethylphenyl)-4,5-dihydro-1H-imidazol-3-ium (carbene D), 4,5-dichloro-1,3-bis(2,6-diisopropylphenyl)-1H-imidazol-3-ium (carbene E), 1,3-di-tert-butyl-1H-imidazol-3-ium (carbene F), and 1,3-ditert-butyl-4,5-dihydro-1H-imidazol-3-ium, said salts being, for example, in the form of chloride salts, as shown below:

or oxygen-containing bases, such as, for example, hydrogen peroxide; benzoyl peroxide; or an alkoxide selected from the methoxide, ethoxide, propoxide, butoxide, pentoxide, or hexoxide of sodium or of potassium.

The organic catalyst is advantageously:

a secondary or tertiary amine selected from triazabicyclodecene (TBD); N-methyltriazabicyclodecene (MeTBD), 1,8-diazabicyclo[5.4.0]undec-7-ene (DBU), trimethylamine, triethylamine, piperidine, 4-dimethylaminopyridine (DMAP), 1,4-diazabicyclo-[2.2.2]octane (DABCO), proline, phenylalanine, a thiazolium salt, N-diisopropylethylamine (DIPEA or DIEA); or an N-heterocyclic carbene such as a carbene obtained from an imidazolium salt selected from the salts of 1,3-bis(2,6-diisopropylphenyl)-1H-imidazol-3-ium (carbene A), 1,3-bis(2,6-diisopropylphenyl)-4,5-dihydro-1H-imidazol-3-ium (carbene C), 1,3-bis(2,4,6-trimethylphenyl)-1H-imidazol-3-ium (carbene B), 1,3-bis(2,4,6-trimethylphenyl)-4,5-dihydro-1H-imidazol-3-ium (carbene D), 4,5-dichloro-1,3-bis(2,6-diisopropylphenyl)-1H-imidazol-3-ium (carbene E), 1,3-di-tert-butyl-1H-imidazol-3-ium (carbene F), and 1,3-ditert-butyl-4,5-dihydro-1H-imidazol-3-ium, said salts being, for example, in the form of chloride salts as shown below:

-continued

According to one preferred variant of the invention, the organic catalyst is selected from triazabicyclodecene (TBD), N-methyltriazabicyclodecene (MeTBD), 1,8-diazabicyclo [5.4.0]undec-7-ene (DBU); or an N-heterocyclic carbene such as a carbene obtained from an imidazolium salt, such as 1,3-bis(2,6-diisopropylphenyl)-1H-imidazol-3-ium (carbene A) chloride, 1,3-bis(2,6-diisopropylphenyl)-4,5-dihydro-1H-imidazol-3-ium (carbene C) chloride, 1,3-di-tert-butyl-1H-imidazol-3-ium chloride, 1,3-di-tert-butyl-4,5-dihydro-1H-imidazol-3-ium (carbene F) chloride, 1,3-bis(2,4,6-trimethylphenyl)-1H-imidazol-3-ium (carbene B) chloride, 1,3-bis(2,4,6-trimethylphenyl)-4,5-dihydro-1H-imidazol-3-ium (carbene D) chloride, and 4,5-dichloro-1,3-bis(2,6-diisopropylphenyl)-1H-imidazol-3-ium (carbene E) chloride.

When the catalyst is a metal catalyst, it may be selected from the salts or complexes of:
  metals selected from boron, silicon, aluminum, gallium, tin, and indium, as for example $Al(OiPr)_3$, $SnCl_2$, and $InBr_3$;
  alkali metals selected from sodium and potassium, as for example $Na_2CO_3$, $K_2CO_3$, and $Cs_2CO_3$;
  alkaline earth metals selected from magnesium and calcium, as for example $MgSO_4$ and $Ca(BH_4)_2$;
  transition metals selected from nickel, iron, cobalt, zinc, copper, rhodium, ruthenium, platinum, palladium, and iridium, as for example $Fe(BH_4)_2 \cdot 6H_2O$, CuCl, and $ZnEt_2$;
  rare earths selected from lanthanum, cerium, praseodymium, and neodymium, as for example $La(OTf)_3$ and $CeCl_3$.

A metal complex is an organometallic compound or inorganic coordination compound in which a metal ion is bonded to an organic or inorganic ligand. An organometallic or inorganic complex may be obtained by mixing a metal salt with a ligand, the ligand bonding to the metal via phosphorus, carbon, nitrogen, oxygen, hydrogen, or silicon atoms, for example. Organic or inorganic ligands include, for example, tris[2-(diphenylphosphino)ethyl]phosphine ($PP_3$), carbene A, and tricyclohexylphosphine.

The metal catalyst is advantageously selected from salts or complexes of transition metals selected from nickel, iron, cobalt, zinc, copper, rhodium, ruthenium, platinum, palladium, and iridium, as for example $Fe(BH_4)_2 \cdot 6H_2O$, CuCl, and $ZnEt_2$.

Figure 2:
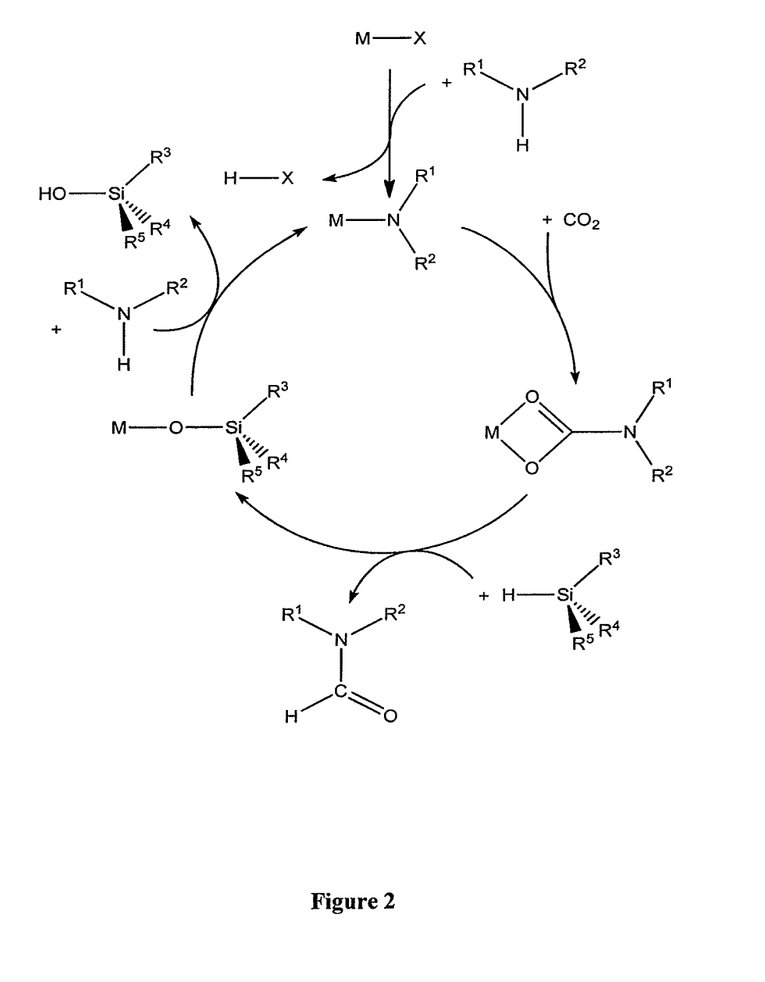
FIG. 2 shows the mechanism of conversion of $CO_2$ in the presence of a metal catalyst.
Figure 3:
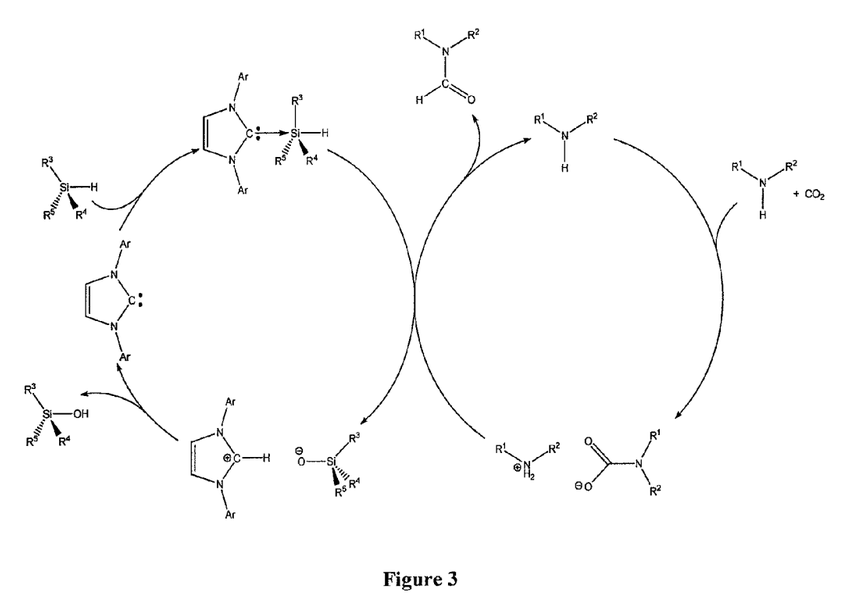
FIG. 3 shows the mechanism of conversion of $CO_2$, by activation of the silane compound, in the presence of a nucleophilic catalyst, such as an N-heterocyclic carbene.

Without wishing to be tied by the theory, in the case of the metal catalysts, the precatalyst reacts with the amine $R^1R^2NH$ to form an amide complex, which is capable of reacting with a molecule of $CO_2$. The resulting metal carbamate is eventually reduced by the silane compound, forming a molecule of the formamide compound and also a silanolate complex. This complex is capable of regenerating the amide catalyst by a sigma metathesis as shown in FIG. 2. In the case of the organic catalysts, especially the organic bases, there are three different possible mechanisms, depending on the nature of the precatalysts:

—Mechanism by Activation of the Silane Compound

Figure 4:
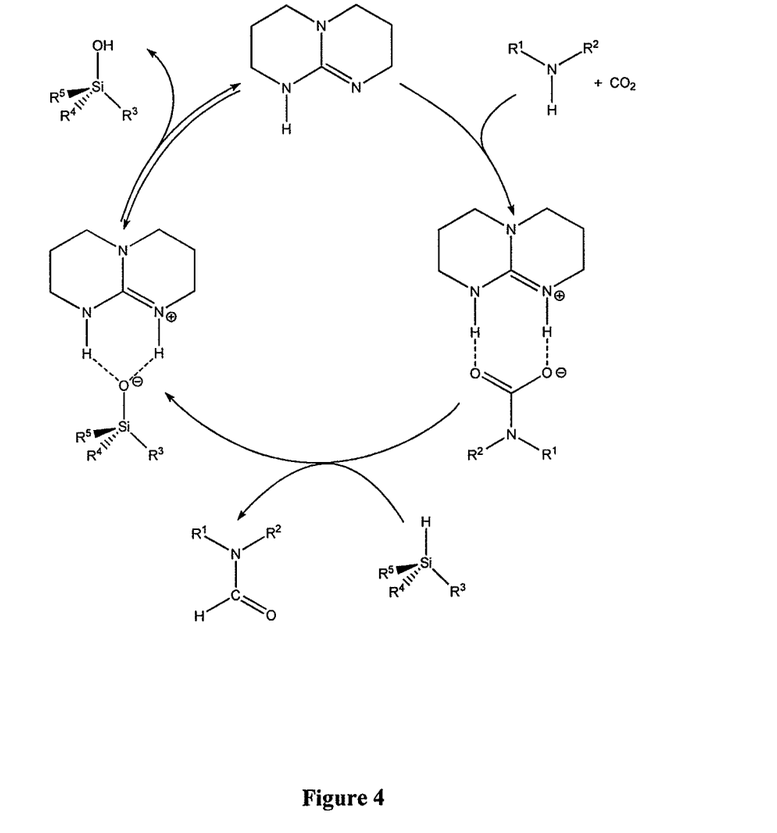
FIG. 4 shows the mechanism of conversion of $CO_2$, by activation of the carbamate, in the presence of a basic catalyst of low nucleophilicity, such as TBD.

This mechanism is followed by nucleophilic catalysts, typically N-heterocyclic carbenes. It is shown in FIG. 3 for the example of an N-heterocyclic carbene;

—Mechanism by Activation of the Carbamate

Figure 5:
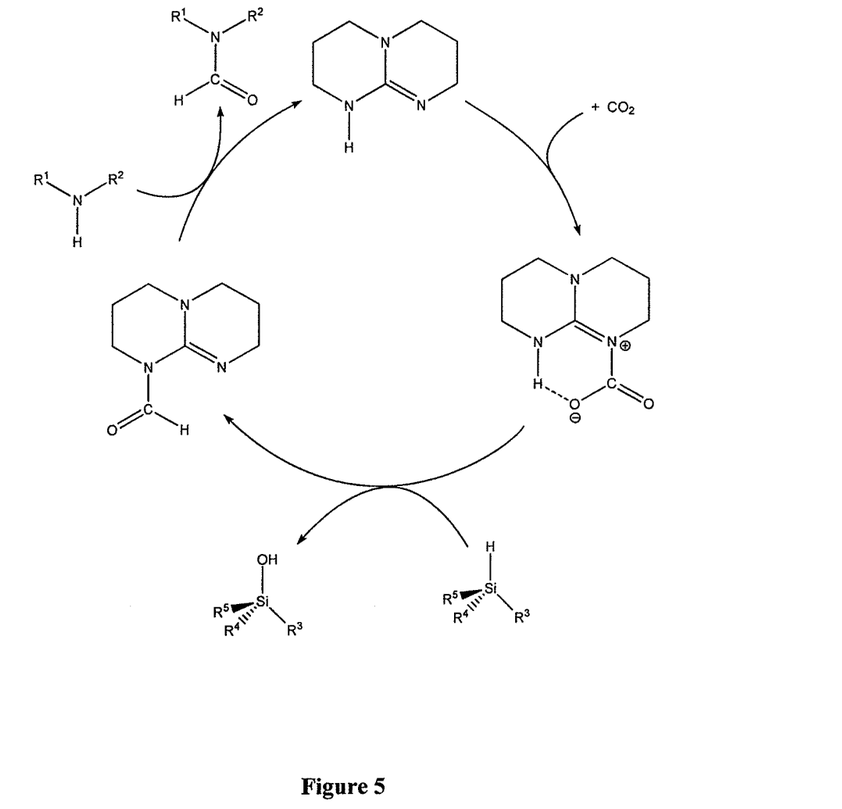
FIG. 5 shows the mechanism of conversion of $CO_2$, by trans-formylation, in the presence of TBD.

This mechanism is followed by basic catalysts of low nucleophilicity, such as TBD, DBU, and Me-TBD especially. It is shown in FIG. 4 for the example of TBD;

—Mechanism by Trans-Formylation

This mechanism is followed by basic catalysts possessing an N—H bond which can be formylated in the presence of $CO_2$ and of a silane compound $R^3R^4R^5SiH$. The formyl function (CHO) is subsequently transferred to the amine substrate $R^1R^2NH$. This catalytic cycle, for example with TBD, has been observed in competition with the catalytic cycle shown in FIG. 4. This mechanism by trans-formylation is shown in FIG. 5 for the example of TBD.

Where appropriate, the catalysts may be immobilized on heterogeneous supports, in order to allow for the catalyst to be easily separated and/or to be recycled. Said heterogeneous supports may be selected from supports based on silica gel or on polymeric plastics such as, for example, polystyrene; carbon supports selected from carbon nanotubes; silicon carbide; alumina; or magnesium chloride ($MgCl_2$).

In the process according to the invention, the reaction may take place under $CO_2$ pressure, by bubbling $CO_2$ into the reaction mixture, or under a dry atmosphere containing $CO_2$ (dried ambient air comprising, for example, approximately 78% by volume of nitrogen, 21% by volume of oxygen, and approximately 0.2% to 0.04% by volume of carbon dioxide). The reaction may also take place using supercritical $CO_2$.

The reaction preferably takes place under $CO_2$ pressure.

The pressure of the $CO_2$ in that case may be between 1 and 50 bar, preferably between 1 and 30, more preferably between 1 and 10 bar, endpoints included.

The temperature of the reaction may be between 25 and 150° C., preferably between 50 and 125° C., more preferably between 70 and 100° C., endpoints included.

The duration of the reaction depends on the conversion rate of the amine of formula (II). The reaction is advantageously maintained until full conversion of the amine of formula (II). The reaction is carried out for a time of 5 minutes to 72 hours, advantageously from 15 minutes to 48 hours, preferably from 1 to 48 hours, endpoints included.

The process of the invention, more particularly the reaction between the different reactants, may take place in one or a mixture of at least two solvents) selected from:
ethers, preferably diethyl ether or THF;
hydrocarbons, preferably benzene or toluene;
nitrogen-containing solvents, preferably pyridine or acetonitrile;
sulfoxides, preferably dimethyl sulfoxide; and
alkyl halides, preferably chloroform or methylene chloride.

According to one preferred variant of the invention, there is no need to add an additional solvent. In this case the amine of the formula (II) is a solvent. Accordingly, in addition to its role in functionalizing the $CO_2$, the amine serves as solvent.

The molar ratio between the silane compound of formula (III) and the amine of formula (II) is from 0.5 to 5, preferably from 1 to 3, endpoints included. The amount of catalyst is from 0.001 to 1 molar equivalent, preferably from 0.01 to 1 molar equivalent, more preferably from 0.01 to 0.9 molar equivalent, more preferably still from 0.01 to 0.5 molar equivalent, endpoints included, relative to the amine of formula (II).

The invention further relates to the process for preparing labeled formamide compounds of formula (I'):

in which
$R_1$ and $R_2$ are as defined before,
H* represents a hydrogen atom ($^1H$), deuterium ($^2H$), or tritium ($^3H$),
O* represents an oxygen atom ($^{16}O$) or an isotope $^{17}O$ or $^{18}O$,
C* represents a carbon atom ($^{12}C$) or an isotope $^{11}C$, $^{13}C$ or $^{14}C$,
N* represents a nitrogen atom ($^{14}N$) or an isotope $^{15}N$,
characterized in that an amine of formula (II') in which $R^1$, $R^2$ and N* are as defined above is reacted with $C^*O_2^*$ in which C* and O* are as defined above, in the presence of a catalyst and of a silane compound of formula (III')

in which
$R^3$, $R^4$, $R^5$, and H* are as defined above.

The compounds of formula (I') in fact correspond to the compounds of formula (I) comprising at least one selected isotope or radiolabel/radiotracer.

Isotopes are, for a given element, two atoms having the same number of protons (and electrons) but a different number of neutrons. Since they have the same number of electrons and protons, the chemical properties of the isotopes of a given element are virtually identical. There may, however, be slight variations in the rate of a chemical reaction when one of the atoms of a reactant is replaced by one of its isotopes. On the other hand, since the nucleus does not contain the same number of neutrons, the mass of the atoms varies and this may make the atom unstable: this is reason that they may be radioactive. In that case they are radioisotopes. In the context of the invention, the term "isotopes" may also encompass "radioisotopes".

Radiolabeling is the combining of a given molecule or compound with an isotope which will allow the development and/or fixation of the molecules to be monitored, in a body, for example. The radiotracer is the radioactive element or elements present within a molecule for following the pathway of that substance, for example, in a body.

This process may therefore open up access to $^{11}C$, $^{13}C$, $^{14}C$, $^{15}N$, $^{2}H$ (D), $^{3}H$ (T), $^{17}O$, and $^{18}O$ labeled formamide compounds.

The use of molecules for purposes of tracing, metabolization, imaging, etc., is detailed in the literature (U. Pleiss, R. Voges, "Synthesis and Applications of Isotopically Labelled Compounds, Volume 7". Wiley-VCH, 2001; R. Voges, J. R. Heys, T. Moenius, "Preparation of Compounds Labeled with Tritium and Carbon-14". Wiley-VCH: Chippenham (UK), 2009). The possibility of forming labeled formamide compounds may be provided by the availability of the corresponding labeled reactants—for example, by:

amines $R^1R^2NH$ enriched in $^{15}N$ are available from $^{15}N$-enriched ammonium chloride: $[^{15}NH_4][Cl]$ (Yong-Joo Kim, Max P. Bernstein, Angela S. Galiano Roth, Floyd E. Romesberg, Paul G. Williard, David J. Fuller, Aidan T. Harrison, and David B. Collum, *J. Org. Chem.* 1991, 56, pp. 4435-4439).

$^{11}C$- or $^{14}C$-labeled $CO_2$ is the principal source of $^{11}C$ and $^{14}C$ and is obtained by acidifying labeled barium carbonate $Ba^{14}CO_3$. (R. Voges, J. R. Heys, T. Moenius, "Preparation of Compounds Labeled with Tritium and Carbon-14". Wiley-VCH: Chippenham (UK), 2009).

$^{17}O$- or $^{18}O$-labeled $CO_2$ is used in synthetic chemistry to produce $^{17}O$- and $^{18}O$-labeled molecules (Christopher J. Dinsmore and Swati P. Mercer, Organic Letters, 2004 Vol., 6, No. 17 2885-2888; John T. Groves and Yoshihito Watanabe, J. Am. Chem. SOC. 1988, 110, pp. 8443-8452).

$^{2}H$-(deuterium or D) or $^{3}H$-(tritium or T) labeled silanes $R^3R^4R^5Si$—H are available from the corresponding chlorosilane $R^3R^4R^5Si$—Cl and from lithium hydride (LiH) or lithium tetrahydridoaluminate ($LiAlH_4$), both the hydrides being available in deuterated and tritiated versions (T. A. Kochina, D. V. Vrazhnov, E. N. Sinotova, V. V. Avrorin, M. Yu. Katsap, and Yu. V. Mykhov, Russian Journal of General Chemistry, Vol. 72, No. 8, 2002, pp. 1222-1224; E. A. Shishigin, V. V. Avrorin, T. A. Kochina, and E. N. Sinotova, Russian Journal of General Chemistry, Vol. 75, No. 1, 2005, p. 152).

Although the labeling of formamide compounds with the nuclei $^{11}C$, $^{13}C$, $^{14}C$, $^{15}N$, $^{2}H$ (D), $^{3}H$ (T), $^{17}O$, and $^{18}O$ is possible, the application directed to the formation of $^{14}C$-labeled molecules may be the most promising in terms of impact and demand.

$^{14}C$-labeled molecules have contributed to numerous advances in the life sciences (enzymatic mechanisms, biosynthetic mechanisms, biochemistry), environmental sciences (tracing of waste), research (elucidation of reaction mechanisms) or else diagnostics, and in research and development into new therapeutic and pharmaceutical products. The reason is that $^{14}C$-labeled molecules have an advantage with regard to metabolic studies, since the $^{14}C$ is readily detectable and quantifiable both in vitro and in vivo.

The principal source of $^{14}C$ is $^{14}CO_2$, which is obtained by acidifying barium carbonate $Ba^{14}CO_3$. The development of processes for synthesizing base molecules used for producing drugs is therefore of prime importance for the production of $^{14}C$-labeled active principles, the metabolism of which may thus be ascertained (R. Voges, J. R. Heys, T. Moenius, "Preparation of Compounds Labeled with Tritium and Carbon-14". Wiley-VCH: Chippenham (UK), 2009).

The major constraint which limits the synthesis of $^{14}C$-labeled molecules is the need to have a high yield of $^{14}C$ product formed, relative to the amount of $^{14}CO_2$ used, and to rely on a limited number of steps, so as to impose a maximum limit on the costs associated with the use of $Ba^{14}CO_3$ (U. Pleiss, R. Voges, "Synthesis and Applications of Isotopically Labelled Compounds, Volume 7". Wiley-VCH, 2001; R. Voges, J. R. Heys, T. Moenius, "Preparation of Compounds Labeled with Tritium and Carbon-14". Wiley-VCH: Chippenham (UK), 2009).

The process according to the invention meets these demands, because the $CO_2$ working pressure can be low, for example from 0.2 to 1 bar. Moreover, the rate of incorporation into $CO_2$ (or yield relative to the $CO_2$ introduced) remains high, and may, for example, exceed 95%.

Lastly, the synthesis of $^{14}C$-labeled formamide compounds according to the present invention is a elegant improvement relative to the known technologies, which generally rely on a minimum of two steps, in which the $CO_2$ is first reduced to formic acid, before being converted into formamide compounds (J. Z. Ho and coll, Helvetica Chimica Acta, 2005, 88, p. 1040). The process of the invention is therefore able to allow access to formamide compounds in a single step, starting from $CO_2$, with good yields and a high selectivity. The advantage of $^{14}C$-labeled formamides in the synthesis of complex $^{14}C$-labeled molecules is illustrated in the following references, in the case of active pharmaceutical principles: J. Z. Ho and coll, Helvetica Chimica Acta, 2005, 88, p. 1040; I. V. Ekhato, S. Bonacorsi Jr., J., Label Compd. Radiopharm, 2011, 54, pp. 202-205; Kenneth K. Chan, James A. Staroscik, Journal of Medicinal Chemistry, 1977, Vol. 20, No. 4, p. 598.

In this variant of the process according to the invention, when the reaction takes place under $CO_2$ pressure, the pressure of the $CO_2$ may in that case be between 0.2 and 50 bar, preferably between 0.2 and 30, more preferably between 0.2 and 10 bar, endpoints included.

The invention further provides for the use of the process for preparing formamide compounds of formula (I) according to the invention in the manufacture of vitamins, pharmaceutical products, glues, acrylic fibers and synthetic leathers, pesticides, and fertilizers.

The invention further provides a method for manufacturing vitamins, pharmaceutical products, glues, acrylic fibers, synthetic leathers, pesticides, and fertilizers, characterized in that it comprises a step of preparing formamide compounds of formula (I) by the process according to the invention.

As already indicated, the process according to the invention leads to the formation of formamide compounds with an excellent yield (of the order of 60% to 100%, for example) and an excellent selectivity (100% of formamide compounds isolated). A simple filtration allows the supported or unsupported catalyst to be recovered, and any silyl-containing byproducts formed to be removed.

BRIEF DESCRIPTION OF THE DRAWINGS

Other advantages and features of the present invention will emerge from a reading of the examples below, which are given by way of illustration and are not limitative, and of the attached figures, in which.

DETAILED DESCRIPTION

EXAMPLES

Example 1

The process for preparing formamide compounds of formula (I) may be carried out according to the following experimental protocol.

Under an inert atmosphere in a glove box, the amine $R^1R^2NH$ (1 molar equivalent), the (pre)catalyst (from 0.001 to 1 molar equivalent), the silane compound (1 equivalent), and the solvent are introduced into a Schlenk tube, which is then sealed with a J. Young tap. The concentration of amine and of silane compound in the reaction mixture is approximately 1M (concentration calculated on the basis of the volume of solvent introduced). The order in which the reactants are introduced is not important.

The Schlenk tube is subsequently placed under $CO_2$ pressure (from 1 to 3 bar) by means of a vacuum ramp, and then is heated to a temperature of between 25 and 100° C. until full conversion of the amine (from 5 minutes to 72 hours of reaction).

When the reaction is at an end, the volatile compounds are removed under reduced pressure and the reaction mixture is purified by chromatography on silica gel. The use of THF as an eluent allows any silyl-containing byproducts to be recovered (mixture of siloxanes and silanols). In a second phase, ethyl acetate is used as the eluent, in order to recover the formamide compound. The ethyl acetate present in the solution thus collected is then removed under reduced pressure, to give the analytically pure formamide compound.

The reaction can be carried out by repeating the experimental protocol described above but using solely the reaction amine as solvent (no addition of solvent to the reaction). In this case, purification is performed by filtration in order to remove the silyl-containing byproduct and the catalyst, which are insoluble in the reaction mixture at ambient temperature. The filtrate recovered contains the pure formamide compound. The reactions tested so far by this experimental protocol have resulted in total conversion of the amine to formamide compound.

An assembly of results is presented below, giving examples of conversions of amines to formamide compounds (determined by NMR), using in a first phase phenylsilane $PhSiH_3$, and subsequently other silanes, depending on the conditions tested. The structures of the amines and of the (pre)catalysts and silanes tested are shown in each case.

The reaction scheme is as follows:

Different (pre)catalysts were tested for the reaction. The results are indicated in table 1.

TABLE 1

| Amine | (Pre)catalyst | Catalyst equivalence | Solvent | Temperature | Time | Conversion |
|---|---|---|---|---|---|---|
| Morpholine | TBD | 5% mol | THF | 75° C. | 24 h | 58% |
| Morpholine | MeTBD | 5% mol | THF | 75° C. | 24 h | 23% |
| Morpholine | DBU | 5% mol | THF | 75° C. | 24 h | 23% |
| Morpholine | carbene A | 5% mol | THF | 75° C. | 24 h | 100% |
| Morpholine | carbene B | 5% mol | benzene | 20° C. | 0.25 h | 69% |
| Morpholine | carbene C | 5% mol | benzene | 20° C. | 0.25 h | 24% |
| Morpholine | carbene D | 5% mol | benzene | 20° C. | 0.25 h | 25% |
| Morpholine | carbene E | 5% mol | benzene | 20° C. | 0.25 h | 35% |
| Morpholine | carbene F | 5% mol | benzene | 20° C. | 0.25 h | 30% |
| Morpholine | $[Fe(BH_4)_2, (H_2O)_6] + PP_3$* | 5% mol | benzene | 100° C. | 24 h | 70% |
| Morpholine | diethyl zinc $Zn(Et)_2$ | 10% mol | benzene | 100° C. | 48 h | 87% |

*$PP_3$ reacts in the presence of the metal salt $[Fe(BH_4)_2,(H_2O)_6]$ to form the metal complex in situ, and said complex acts as catalyst.

The results show that under the operating conditions indicated in table I, the most active (pre)catalysts are TBD, carbene A, carbene B, and the metal complexes. For the other (pre)catalysts, optimization of the operating conditions may be envisaged.

Different solvents were also tested. The results, under the operating conditions described, are indicated in table 2.

TABLE 2

| Amine | (Pre)catalyst | Catalyst | Solvent | Temperature | Time | Conversion |
|---|---|---|---|---|---|---|
| Morpholine | TBD | 5% mol | THF | 100° C. | 24 h | 65% |
| Morpholine | TBD | 5% mol | benzene | 100° C. | 24 h | 70% |
| Morpholine | TBD | 5% mol | DMSO | 100° C. | 24 h | 74% |
| Morpholine | TBD | 5% mol | $CH_3CN$ | 100° C. | 24 h | 93% |
| Morpholine | TBD | 5% mol | no solvent | 100° C. | 24 h | 100% |

The reaction was tested on amines having different electronic structures and steric hindrances. The results are indicated in table 3.

TABLE 3

| Amine | (Pre)catalyst | Catalyst equivalence | Solvent | Temperature | Time | Conversion |
|---|---|---|---|---|---|---|
| Morpholine | TBD | 5 mol % | benzene | 100° C. | 24 h | 70% |
| Diisopropylamine | TBD | 5 mol % | benzene | 100° C. | 24 h | 43% |
| Piperidine | TBD | 5 mol % | benzene | 100° C. | 24 h | 42% |
| Diethylamine | TBD | 5 mol % | benzene | 100° C. | 24 h | 48% |
| p-Butylaniline | TBD | 5 mol % | benzene | 100° C. | 24 h | 50% |
| Morpholine | carbene A | 5 mol % | THF | 20° C. | 0.25 h | 100% |
| Piperidine | carbene A | 5 mol % | THF | 20° C. | 0.5 h | 100% |
| Diethylamine | carbene A | 5 mol % | THF | 20° C. | 1.5 h | 100% |
| Imidazole | carbene A | 5 mol % | THF | 20° C. | 3 h | 80% |
| Benzylamine | carbene A | 5 mol % | THF | 20° C. | 6 h | 60% |
| tert-Butylamine | carbene A | 5 mol % | THF | 20° C. | 2 h | 100% |
| n-Heptylamine | carbene A | 5 mol % | THF | 20° C. | 22 h | 100% |
| p-Butylaniline | carbene A | 5 mol % | THF | 20° C. | 16 h | 100% |
| 2,6-Diisopropyl-aniline | carbene A | 5 mol % | THF | 100° C. | 12 h | 95% |
| Dimethylamine | carbene A | 5 mol % | THF | 20° C. | 24 h | 99% |
| Aniline | carbene A | 5 mol % | THF | 20° C. | 24 h | 35% |
| Diphenylmethan-imine | carbene A | 5 mol % | THF | 20° C. | 24 h | 60% |
| 1,1-Diphenyl-hydrazine | carbene A | 5 mol % | THF | 20° C. | 24 h | 66% |
| Diphenylmethanone hydrazone | carbene A | 5 mol % | THF | 20° C. | 24 h | 40% |
| 1H-Imidazole | carbene A | 5 mol % | THF | 20° C. | 24 h | 99% |
| 1,4,5,6-Tetra-hydropyrimidine | carbene A | 5 mol % | THF | 20° C. | 24 h | 99% |
| 1H-1,2,4-Triazole | carbene A | 5 mol % | THF | 20° C. | 24 h | 10% |
| 3,5-dimethyl-1H-pyrazole | carbene A | 5 mol % | THF | 20° C. | 24 h | 48% |

For certain amines, optimization of the operating conditions may be envisaged.

The reaction was subsequently tested on silanes having different electronic structures and different steric hindrances. The various reactions were carried out in benzene as solvent and at a temperature of 20° C. Optimization of the operating conditions may be envisaged for certain reactions.

TABLE 4

| Amine | Catalyst | Catalyst equivalence | Silane | Silane equivalence | Time | Conversion |
|---|---|---|---|---|---|---|
| Morpholine | carbene A | 5 mol % | (EtO)$_3$SiH | 3 eq. | 24 h | 28% |
| Morpholine | carbene A | 5 mol % | TMDS | 1.5 eq. | 24 h | 43% |
| Morpholine | carbene A | 5 mol % | PMHS | 3 eq. | 24 h | 90% |
| Dimethylamine | carbene A | 5 mol % | PMHS | 3 eq. | 24 h | 90% |
| n-Heptylamine | carbene A | 5 mol % | PMHS | 3 eq. | 24 h | 67% |
| Benzylamine | carbene A | 5 mol % | PMHS | 9 eq. | 24 h | 70% |
| Aniline | carbene A | 5 mol % | PMHS | 3 eq. | 24 h | 83% |
| Diphenylmethanimine | carbene A | 5 mol % | PMHS | 3 eq. | 24 h | 35% |
| 1,1-Diphenyl-hydrazine | carbene A | 5 mol % | PMHS | 3 eq. | 24 h | 83% |
| 3,5-Dimethyl-1H-pyrazole | carbene A | 5 mol % | PMHS | 3 eq. | 24 h | 29% |

The number of molar equivalents of silane indicated is relative to the amine.
The abbreviations used in the tables are as follows:

These results show that the preparation of formamide compounds for the process of the invention is sufficiently flexible for efficient conversion of a wide variety of amines with an excellent selectivity: primary and secondary, aliphatic, aromatic, and heterocyclic amines into formamide compounds, under gentle $CO_2$ pressure conditions and gentle reaction temperatures.

More particularly, in the absence of solvent, the preparation of the formamide compounds according to the process of the invention takes place with an excellent yield and an excellent selectivity.

Example 2

Synthesis of a $^{14}$C-Labeled Phosphodiesterase-4 (PDE-4) Inhibitor

Synthesis of the $^{14}$C-Labeled Formamide Compound

The formamide compound of formula $Bu_2N^{14}CHO$ was synthesized according to the experimental protocol indicated in example 1, using labeled $CO_2$ obtained by the process described by R. Voges, J. R. Heys, T. Moenius, "Preparation of Compounds Labeled with Tritium and Carbon-14". Wiley-VCH: Chippenham (UK), 2009, and under the same conditions in terms of catalyst, solvent, temperature, and time as those indicated for diisopropylamine (table 3).

Synthesis of a $^{14}$C-Labeled Phosphodiesterase-4 (PDE-4) Inhibitor

The formamide compound of formula $Bu_2N^{14}CHO$ was then used in the synthesis of phosphodiesterase-4 (PDE-4) according to the synthesis described by J. Z. Ho and coll., Helvetica Chimica Acta, 2005, 88, p. 1040.

Example 3

Synthesis of $^{14}$C-Labeled Irbesartan

Synthesis of $^{14}$C-Labeled Dimethylformamide

The labeled dimethylformamide of formula $(CH_3)_2N^{14}CHO$ was synthesized according to the experimental protocol indicated in example 1, using labeled $CO_2$ obtained by the process described by R. Voges, J. R. Heys, T. Moenius, "Preparation of Compounds Labeled with Tritium and Carbon-14". Wiley-VCH: Chippenham (UK), 2009, and under the same conditions in terms of catalyst, (carbene A), solvent, temperature, and time as those indicated for diethylamine (table 3).

Synthesis of $^{14}$C-Labeled Irbesartan (Antihypertensive Drug)

The labeled dimethylformamide of formula $(CH_3)_2N^{14}CHO$ was then used in the synthesis of irbesartan according to the synthesis described by I. V. Ekhato, S. Bonacorsi Jr., J., Label Compd. Radiopharm, 2011, 54, pp. 202-205.

Example 4

Synthesis of $^{14}$C-Labeled 5-Azacytidine

Synthesis of $^{14}$C-Labeled Dimethylformamide

The labeled dimethylformamide of formula $(CH_3)_2N^{14}CHO$ was synthesized according to the protocol of example 2.

Synthesis of $^{14}$C-Labeled 5-Azacytidine (Antitumor and Antileukemia Agent)

The labeled dimethylformamide of formula $(CH_3)_2N^{14}CHO$ was subsequently used in the synthesis of 5-azacytidine according to the synthesis described by Kenneth K. Chan, James A. Staroscik, Journal of Medicinal Chemistry, 1977, Vol. 20, No. 4, p. 598.

The invention claimed is:

1. A process for preparing formamide compounds of formula (I):

(I)

in which

R$^1$ and R$^2$ represent independently of one another a hydrogen atom, an alkyl group, an alkenyl group, an alkynyl group, an aryl group, a heteroaryl group, a heterocycle, a silyl group, a siloxy group, an amino group, an aldimine of formula —N═CHR$^6$, or a ketimine of formula —N═CR$^6$R$^7$, said alkyl, alkenyl, alkynyl, aryl, heteroaryl, heterocycle, silyl, siloxy, and amino groups being optionally substituted, or R$^1$ and R$^2$, together with the nitrogen atom to which they are bonded, form an optionally substituted heterocycle, or R$^1$ and R$^2$, with the nitrogen atom to which they are bonded, form a carbon-nitrogen double bond (N═C), thus giving an aldimine of formula —N═CHR$^6$ or a ketimine of formula —N═CR$^6$R$^7$, and

R$^6$ and R$^7$ represent independently of one another a hydrogen atom, an alkyl group, an alkenyl group, an akynyl group, an aryl group, a heteroaryl group, a heterocycle, a silyl group, a siloxy group, or an amino group, said alkyl, alkenyl, akynyl, aryl, heteroaryl, heterocycle, silyl, siloxy, and amino groups being optionally substituted, characterized in that an amine of formula (II) in which R$^1$ and R$^2$ are as defined above, (II)

is reacted with $CO_2$ in the presence of a catalyst and with a silane compound of formula (III)

(III)

in which

R$^3$, R$^4$ and R$^5$ represent independently of one another a hydrogen atom, a halogen atom, a hydroxyl group, an alkyl group, an alkenyl group, an alkynyl group, an alkoxy group, a silyl group, a siloxy group, an aryl group, or an amino group, said alkyl, alkenyl, alkynyl, alkoxy, silyl, siloxy, aryl, and amino groups being optionally substituted, or R$^5$ is as defined above and R$^3$ and R$^4$, together with the silicon atom to which they are bonded, form an optionally substituted, silyl-containing heterocycle.

2. The process as claimed in claim 1, wherein in the amine of formula (II), R$^1$ and R$^2$ represent independently of one another a hydrogen atom, an alkyl group, an aryl group, a heteroaryl group or an amino group, said alkyl, amino, aryl, and heteroaryl groups being optionally substituted, or R$^1$ and R$^2$, together with the nitrogen atom to which they are bonded, form an optionally substituted heterocycle; or R$^1$ and R$^2$, with the nitrogen atom to which they are bonded, form a carbon-nitrogen double bond (N═C), thus giving an aldimine of formula —N═CHR$^6$ or a ketimine of formula —N═CR$^6$R$^7$, in which R$^6$ and R$^7$ represent independently of one another a hydrogen atom, an alkyl group, an aryl group, a heteroaryl group, or a heterocycle, said alkyl, aryl, heteroaryl, and heterocycle groups being optionally substituted.

3. The process as claimed in claim 1, wherein in the silane compound of formula (III), R$^3$, R$^4$ and R$^5$ represent independently of one another a hydrogen atom, an alkyl group, an alkoxy group, an aryl group, a silyl group, or a siloxy group, said alkyl, alkoxy, silyl, siloxy, and aryl groups being optionally substituted.

4. The process as claimed in claim 1, wherein the catalyst is selected from organic catalysts or metal catalysts selected from metal complexes or salts.

5. The process as claimed in claim 4, wherein the organic catalyst is:

a secondary or tertiary amine selected from triazabicyclodecene (TBD); N-methyltriazabicyclodecene (MeTBD), 1,8-diazabicyclo[5.4.0]undec-7-ene (DBU), trimethylamine, triethyleamine, piperidine, 4-dimethylaminopyridine (DMAP), 1,4-diazabicyclo[2.2.2]octane (DABCO), proline, phenylalanine, a thiazolium salt, N-diisopropylethylamine (DIPEA or DIEA); or an N-heterocyclic carbene such as a carbene obtained from an imidazolium salt selected from the salts of 1,3-bis(2,6-diisopropylphenyl)-1H-imidazol-3-ium (carbene A), 1,3-bis(2,6-diisopropylphenyl)-4,5-dihydro-1H-imidazol-3-ium (carbene C), 1,3-bis(2,4,6-trimethylphenyl)-1H-imidazol-3-ium (carbene B), 1,3-bis(2,4,6-trimethylphenyl)-4,5-dihydro-1H-imidazol-3-ium (carbene D), 4,5-dichloro-1,3-bis(2,6-diisopropylphenyl)-1H-imidazol-3-ium (carbene E), 1,3-di-tert-butyl-1H-imidazol-3-ium (carbene F), and 1,3-di-tert-butyl-4,5-dihydro-1H-imidazol-3-ium, said salts being in the form of chloride salts.

6. The process as claimed in claim 4, wherein the metal catalyst is selected from salts or complexes of transition metals selected from nickel, iron, cobalt, zinc, copper, rhodium, ruthenium, platinum, palladium, and iridium, as for example $Fe(BH_4)_2 \cdot 6H_2O$, CuCl, and $ZnEt_2$.

7. The process as claimed in claim 1, wherein the reaction is carried out under a $CO_2$ pressure of between 1 and 50 bar, endpoints included.

8. The process as claimed in claim 1, wherein the reaction is carried out at a temperature of between 25 and 150° C., endpoints included.

9. The process as claimed in claim 1, wherein the reaction is carried out for a time of 5 minutes to 72 hours, endpoints included.

10. The process as claimed in claim 1, wherein the reaction is carried out in one or a mixture of at least two solvent(s) selected from:
- ethers, preferably diethyl ether or THF;
- hydrocarbons, preferably benzene or toluene;
- nitrogen-containing solvents, preferably pyridine or acetonitrile;
- sulfoxides, preferably dimethyl sulfoxide; and
- alkyl halides, preferably chloroform or methylene chloride.

11. The process as claimed in claim 1, wherein the solvent is the amine of formula (II).

12. The process as claimed in claim 1, wherein the molar ratio between the silane compound of formula (III) and the amine of formula (II) is from 0.5 to 5, endpoints included.

13. The process as claimed in claim 1, wherein the amount of catalyst is from 0.001 to 1 molar equivalent, endpoints included, relative to the amine of formula (II).

14. The use of a process for preparing formamide compounds of formula (I) as claimed in claim 1 in the manufacture of vitamins, pharmaceutical products, glues, acrylic fibers, synthetic leathers, pesticides, and fertilizers.

15. The process as claimed in claim 1 wherein the reaction is carried out at a temperature of between 50 and 125° C., endpoints included.

16. The process as claimed in claim 1, wherein the reaction is carried out at a temperature of between 70 and 100° C., endpoints included.

17. The process as claimed in claim 1, wherein the reaction is carried out for a time of 15 minutes to 48 hours, preferably of 1 to 48 hours, endpoints included.

18. The process as claimed in claim 1, wherein the reaction is carried out for a time of 1 to 48 hours, endpoints included.

19. The process as claimed in claim 1, wherein the molar ratio between the silane compound of formula (III) and the amine of formula (II) is from 1 to 3, endpoints included.

20. The process as claimed in claim 1, wherein the amount of catalyst is from 0.01 to 0.9 molar equivalent, endpoints included, relative to the amine of formula (II).

* * * * *